United States Patent
Beeckler et al.

(10) Patent No.: US 11,116,942 B2
(45) Date of Patent: Sep. 14, 2021

(54) MEDICAL DEVICE SHAFT WITH REDUCED WHIPPING

(71) Applicant: Biosense Webster (Israel) Ltd., Yokneam (IL)

(72) Inventors: Christopher Thomas Beeckler, Brea, CA (US); Maribeth Esguerra Wilczynski, Irwindale, CA (US); Joseph Thomas Keyes, Sierra Madre, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 100 days.

(21) Appl. No.: 16/235,405

(22) Filed: Dec. 28, 2018

(65) Prior Publication Data

US 2020/0206464 A1 Jul. 2, 2020

(51) Int. Cl.
*A61M 25/01* (2006.01)
*A61B 5/00* (2006.01)
*A61B 17/00* (2006.01)

(52) U.S. Cl.
CPC ....... *A61M 25/0147* (2013.01); *A61B 5/6852* (2013.01); *A61B 2017/00327* (2013.01); *A61M 2025/015* (2013.01)

(58) Field of Classification Search
CPC ........ A61M 25/0147; A61M 2025/015; A61M 25/0009; A61M 25/0136; A61B 5/6852; A61B 2017/00327; A61B 2025/015; A61B 2017/00323; A61B 2018/00577; A61B 2017/003; A61B 18/1492; A61B 2018/00375; A61B 2018/00357; A61B 2018/00351
See application file for complete search history.

(56) References Cited

U.S. PATENT DOCUMENTS

| 6,183,463 B1 | 2/2001 | Webler, Jr. |
| 6,571,131 B1 * | 5/2003 | Nguyen ............. A61B 18/1492 607/122 |
| 2002/0165461 A1 | 11/2002 | Hayzelden et al. |
| 2005/0070844 A1 | 3/2005 | Chow et al. |

(Continued)

FOREIGN PATENT DOCUMENTS

| EP | 2540245 A1 | 1/2013 |
| EP | 2559450 A1 | 2/2013 |
| WO | 20029135251 A1 | 11/2009 |

OTHER PUBLICATIONS

Extended European Search Report issued in corresponding European Patent Application No. 19 21 9622 dated Jun. 3, 2020.

*Primary Examiner* — Theodore J Stigell
*Assistant Examiner* — Rachel T. Smith
(74) *Attorney, Agent, or Firm* — Troutman Pepper Hamilton Sanders LLP

(57) ABSTRACT

A medical probe, including a flexible insertion tube having a proximal segment and a deflectable distal segment, and containing first and second lumens running longitudinally through the insertion tube, wherein the first and second lumens are twisted around each other in the proximal segment, and run parallel to each other in the deflectable distal segment. The medical probe also includes first and second wires running respectively through the first and second lumens and having respective first and second distal ends, which are anchored within the deflectable distal segment of the insertion tube.

20 Claims, 3 Drawing Sheets

(56) References Cited

U.S. PATENT DOCUMENTS

| | | |
|---|---|---|
| 2006/0184106 A1 | 8/2006 | McDaniel et al. |
| 2010/0057050 A1 | 3/2010 | Webler, Jr. |
| 2016/0022961 A1* | 1/2016 | Rosenman ........ A61M 25/0141 604/95.04 |
| 2017/0106170 A1* | 4/2017 | Hsueh ............... A61M 25/0147 |

* cited by examiner

MEDICAL DEVICE SHAFT WITH REDUCED WHIPPING

FIELD OF THE INVENTION

The present invention relates generally to invasive probes, and specifically to a medical probe having a deflectable distal segment.

BACKGROUND OF THE INVENTION

Some medical procedures, such as mapping a cavity of a body organ (e.g., a heart), are performed by inserting a medical probe into the cavity. In some configurations, the medical probe comprises a distal segment that can be deflected along a plane. The deflection (i.e., along with extension, retraction and rotation of the medical probe) enables a distal tip of the deflectable distal segment to engage tissue at different locations in the body cavity.

In additional configurations, the medical probe can deliver radio frequency (RF) current to ablate tissue in contact with the probe's distal end in order to provide a therapeutic result. In alternative configurations, the medical probe can deliver a different energy source such as laser, ultrasound, or cryogenic cooling in order to provide the therapeutic result.

U.S. Patent Application 2010/0057050 to Webler describes a catheter configured for incremental rotation. The catheter includes a shaft having a distal section that comprises incremental rotation inducing features that minimize whipping of the shaft as the shaft is rotated. An example of the incremental rotation inducing features comprises two or more longitudinal shaft portions of a lower flexural modulus circumferentially spaced apart around the shaft.

U.S. Patent Application 2005/0070844 to Chow et al. describes a deflectable catheter. The catheter includes a shaft having a proximal section and a distal section that is more flexible than the proximal section. The catheter also includes a needle assembly and a tendon disposed within a lumen that is approximately centrally located within the shaft at the proximal section, and is located off-center of the shaft at the distal section. In some embodiments, the tendon and the needle assembly are twisted about each other.

U.S. Patent Application 2002/0165461 to Hayzelden et al. describes a steerable catheter with shaft support system for resisting axial compressive loads. The catheter has a relatively flexible distal-end region, and includes a torque transfer system to enhance torque transfer from the handle to the distal tip. The torque transfer system includes a flat ribbon within the relatively flexible distal-end region to enhance torque transfer through the distal-end region of the catheter.

U.S. Pat. No. 6,183,463 to Webster describes a bidirectional steerable catheter with a bidirectional control handle. The catheter includes a thermocouple formed by a wire pair. The wires of the wire pair are electrically isolated from each other (except at their distal ends), are twisted together, and are covered with a short piece of plastic tubing and covered with epoxy.

U.S. Patent Application 2006/0184106 to McDaniel et al. describes a steerable catheter with in-plane deflection. The catheter has a tip section at a distal end of the catheter body that includes flexible plastic tubing having a pair of diametrically-opposed lumens. The catheter also includes two puller wires, each of the wires extending through one of the pair of lumens in the tip section and through the catheter body, anchored to a control handle at its proximal end, and anchored to the tip section at its distal end.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention, a medical probe including a flexible insertion tube having a proximal segment and a deflectable distal segment, and containing first and second lumens running longitudinally through the insertion tube, wherein the first and second lumens are twisted around each other in the proximal segment, and run parallel to each other in the deflectable distal segment, and first and second wires running respectively through the first and second lumens and having respective first and second distal ends, which are anchored within the deflectable distal segment of the insertion tube.

In one embodiment, the medical probe also includes first and second compression coils that respectively contain the first and the second wires and respectively include the first and the second lumens. In additional embodiments, the medical probe further includes first and second tubular structures that respectively contain the first and the second compression coils.

In another embodiment, the medical probe further includes a third lumen running longitudinally through the insertion tube, wherein the first lumen, the second lumen and the third lumen are twisted around each other in the proximal segment. In supplemental embodiments, the medical probe also includes one or more functional elements running through the third lumen, wherein a given functional element is selected from a list consisting of an additional wire, a cable, and an irrigation line.

In some embodiments, pulling on each of the wires deflects the deflectable distal segment in different respective directions. In one embodiment, the first and second lumens twisted around each other in the proximal segment limit whipping of the probe as it is rotated. In another embodiment, the first and the second wires include respective first and second proximal ends, and the medical probe also includes a handle coupled to the first and second proximal ends in order to control the pulling on the wires. In an additional embodiment, the deflection is in a two-dimensional plane.

In further embodiments, the first and second ends of the wires are respectively anchored at different, respective points within the deflectable distal segment of the insertion tube.

There is also provided, in accordance with an embodiment of the present invention, a method for fabricating a medical probe, including providing a flexible insertion tube having a proximal segment and a deflectable distal segment, and containing first and second lumens running longitudinally through the insertion tube, wherein the first and second lumens are twisted around each other in the proximal segment, and run parallel to each other in the deflectable distal segment, and running first and second wires respectively through the first and second lumens, the first and the second wires having respective first and second distal ends, which are anchored within the deflectable distal segment of the insertion tube.

BRIEF DESCRIPTION OF THE DRAWINGS

The disclosure is herein described, by way of example only, with reference to the accompanying drawings, wherein.

DETAILED DESCRIPTION OF EMBODIMENTS

Embodiments of the present invention describe a medical probe having a flexible insertion tube that comprises a proximal segment and a deflectable distal segment. The medical probe contains first and second lumens running longitudinally through the insertion tube, wherein the first and second lumens are twisted around each other in the proximal segment, and run parallel to each other in the deflectable distal segment. Proximally, the lumens are formed by hollow coils surrounded by polymer tubes. These coils, referred to as "compression coils" are secured in a compressed manner so that the coil is bottomed out, allowing the compression coil to have high axial strength, but with far greater flexibility than a metal tube. The medical probe also comprises first and second wires running respectively through the first and second lumens, the wires having respective first and second distal ends, which may be anchored at different, respective points within the deflectable distal segment of the insertion tube.

During a medical procedure, the proximal segment may be forced to take a curve by a sheath or by the anatomy. If the compression coils run parallel down the length of the proximal segment, then the proximal segment may have a rotationally dependent stiffness. As a result of this stiffness, whipping (i.e., undesired rotational movement of the distal section) may occur when the proximal segment of the probe is torqued (i.e., rotated) by a medical professional. This can cause difficulties for the probe to reach and to remain stable in certain locations of the anatomy, and there may be potential safety concerns due to unintended catheter movement, especially during delivery of therapy. In medical probes implementing embodiments of the present invention, the compression coils are twisted around each other in the proximal segment. As a result, the proximal segment of the probe is rotationally symmetrical, and has no preferential direction of bending. Therefore, distal segments of medical probes implementing embodiments of the present invention typically have minimal whipping when torqued by a medical professional.

System Description

Figure 1:
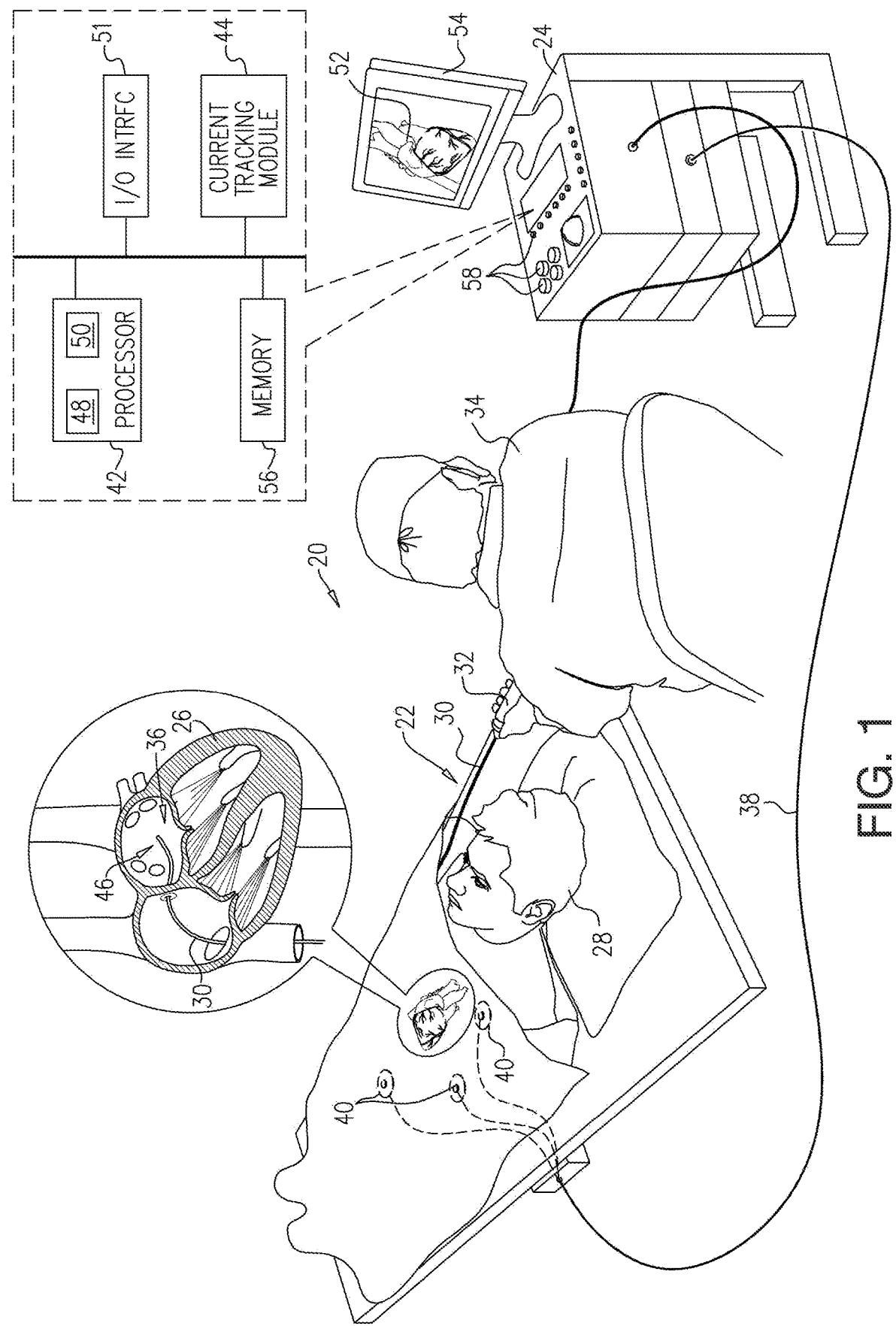
FIG. 1 is a schematic, pictorial illustration of a medical system comprising a medical probe having a deflectable distal section, in accordance with an embodiment of the present invention.

FIG. 1 is a schematic, pictorial illustration of a medical system 20 comprising medical probe 22 and a control console 24, in accordance with an embodiment of the present invention. Medical system 20 may be based, for example, on the CARTO® system, produced by Biosense Webster Inc. of 33 Technology Drive, Irvine, Calif. 92618 USA. In embodiments described hereinbelow, medical probe 22 can be used for diagnostic or therapeutic treatment, such as for mapping electrical potentials in a heart 26 of a patient 28. Alternatively, medical probe 22 may be used, mutatis mutandis, for other therapeutic and/or diagnostic purposes in the heart or in other body organs.

Probe 22 comprises an insertion tube 30 and a handle 32 coupled to a proximal end of the insertion tube. By manipulating handle 32, a medical professional 34 can insert probe 22 into a body cavity in patient 28. For example, medical professional 34 can insert probe 22 through the vascular system of patient 28 so that a distal end 36 of probe 22 enters a chamber of heart 26 and engages endocardial tissue at a desired location or locations.

Control console 24 is connected, by a cable 38, to body surface electrodes, which typically comprise adhesive skin patches 40 that are affixed to patient 28. Control console 24 comprises a processor 42 that, in conjunction with a current tracking module 44, determines position coordinates of distal end 36 inside heart 26 based on impedances and/or currents measured between adhesive skin patches 40 and an electrode 46 that is affixed to distal end 36. In addition to being used as a location sensor during a medical procedure, electrode 46 may perform other tasks such as measuring electrical activity of heart 26.

As stated above, in conjunction with current tracking module 44, processor 42 may determine position coordinates of distal end 36 inside heart 26 based on impedances and/or currents measured between adhesive skin patches 40 and electrode 46. Such a determination is typically after a calibration process relating the impedances or currents to known positions of the distal end has been performed. In some embodiments, electrode 46 can be configured to apply a signal to tissue in heart 26, and/or to measure a certain physiological property (e.g., the local surface electrical potential) at a location in the heart.

Processor 42 may comprise real-time noise reduction circuitry 48 typically configured as a field programmable gate array (FPGA), followed by an analog-to-digital (A/D) signal conversion integrated circuit 50. The processor can pass the signal from A/D circuit 50 to another processor and/or can be programmed to determine the position coordinates referred to above.

Although the medical system shown in FIG. 1 uses impedance or current-based sensing to measure a location of distal end 36, other position tracking techniques may be used (e.g., techniques using magnetic-based sensors). Impedance and current-based position tracking techniques are described, for example, in U.S. Pat. Nos. 5,983,126, 6,456,864 and 5,944,022. The methods of position sensing described hereinabove are implemented in the above-mentioned CARTO® system and are described in detail in the patents cited above.

Control console 24 also comprises an input/output (I/O) communications interface 51 that enables the control console to transfer signals from, and/or transfer signals to electrode 46 and adhesive skin patches 40. Based on signals received from electrode 46 and adhesive skin patches 40, processor 42 can generate a map 52 that shows the position of distal end 36 in the patient's body. During the procedure, processor 42 can present map 52 to medical professional 34 on a display 54, and store data representing the map in a memory 56. Memory 56 may comprise any suitable volatile and/or non-volatile memory, such as random access memory or a hard disk drive. In some embodiments, medical professional 34 can manipulate map 52 using one or more input devices 58. In alternative embodiments, display 54 may comprise a touchscreen that can be configured to accept inputs from medical professional 34, in addition to presenting map 52.

Figure 2:
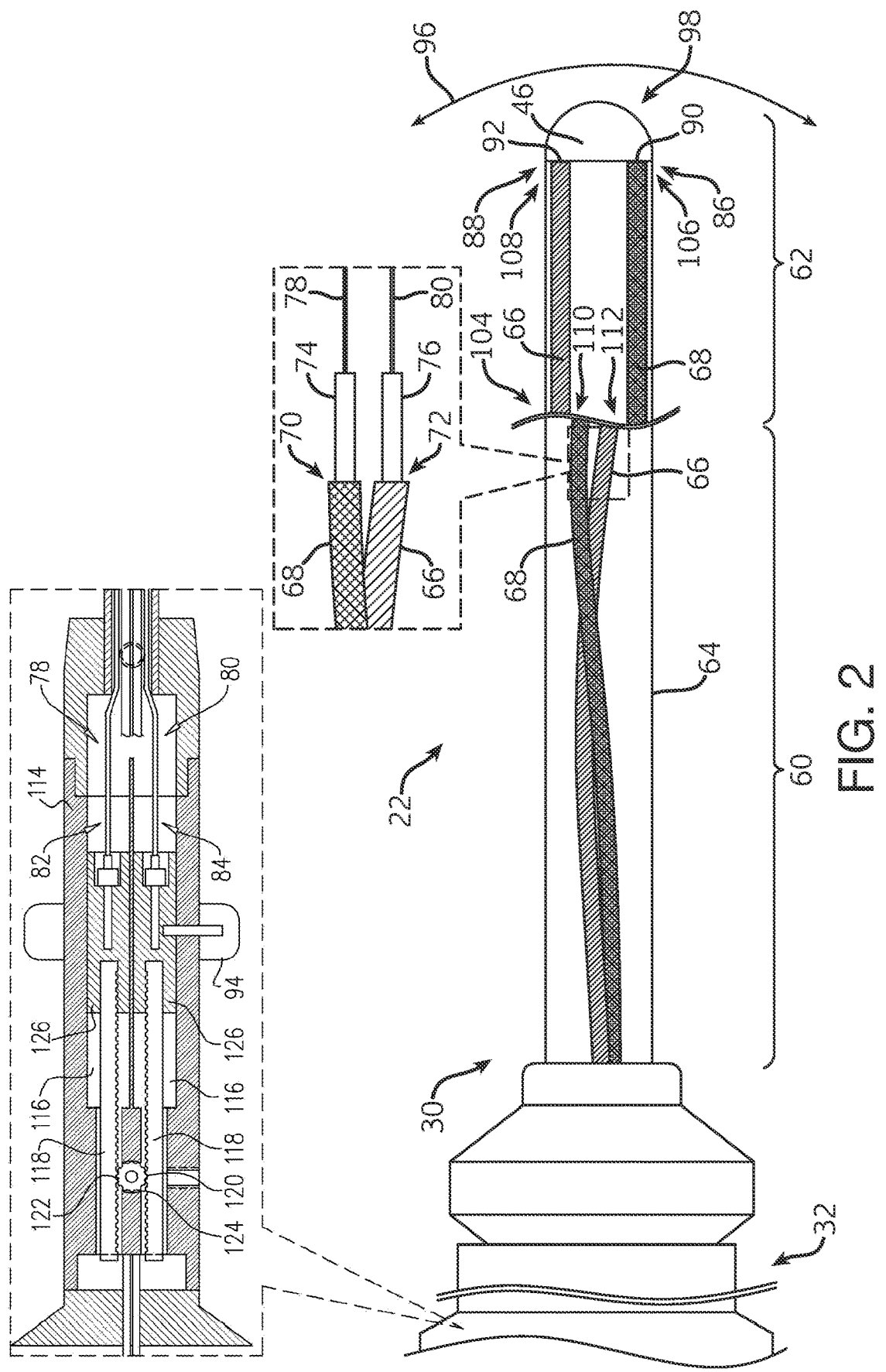
FIG. 2 is a schematic cutaway longitudinal view of the medical probe, in accordance with an embodiment of the present invention.

FIG. 2 is a schematic cutaway longitudinal view of probe 22, in accordance with an embodiment of the present invention. Insertion tube 30 comprises a proximal segment 60 and a deflectable distal segment 62 that are both covered by a biocompatible flexible material 64. Distal segment 62 comprises a proximal end 104.

Insertion tube 30 comprises a pair of tubular structures (also referred to herein simply as tubes) 66 and 68 that run longitudinally within insertion tube 30 and comprise respective lumens 70 and 72. Lumens 70 and 72 (i.e., tubes 66 and 68) are twisted around each other within proximal segment 60, and run parallel to each other within deflectable distal segment 62. In some embodiments, distal segment 62 may be formed by an extrusion process, and the lumens may be formed in the extrusion as separate tubes which are larger than proximal tubes. During assembly the smaller diameter proximal tubes may be bonded within the larger diameter distal tubes creating an uninterrupted lumen. In embodiments of the present invention, the term parallel to each other indicates that the lumens are parallel to within a predefined tolerance, for example 10 degrees, 5 degrees or 2 degrees.

Probe 22 also comprises a pair of compression coils 74 and that have respective distal ends 106 and 108, and are respectively contained within tubes 66 and 68. In one embodiment, compression coils 74 and 76 are respectively secured to proximal ends 110 and 112 of the lumens in segment 62 with a bonding material such as polyurethane adhesive or epoxy (not shown). Between these securing locations and distal ends 106 and 108, each of the compression coils can be formed so as not to be bottomed out. This allows any unsecured segments of the compression coils in distal segment 62 to compress during deflection and not inhibit movement. Alternatively, compression coils 74 and 76 may be terminated in a proximal securing location (e.g., location 110 and/or location 112), and low friction flexible tubes (not shown) can be placed over the puller wires. In this embodiment, the length of flexible tubes can be chosen to be between 1 mm-5 mm shorter than the distance between securing locations 110 and 112 and distal locations 106 and 108, thus ensuring that the flexible tubes do not inhibit desired deflection. Probe 22 additionally comprises a pair of puller wires 78 and 80 that are respectively contained within coils 74 and 76, and have respective proximal ends 82 and 84, and respective distal ends 86 and 88.

In one embodiment, distal ends 86 and 88 are respectively anchored to points 90 and 92 in distal segment 62 of probe 22. In another embodiment, distal ends 86 and 88 can be respectively anchored to a single point (e.g., point 90 or 92) in distal segment 62 of probe 22.

In alternative embodiments, insertion tube 30 can be configured to implement embodiments of the present invention without tubes 66 and 68. In this alternative embodiment, the compression coils are twisted around each other in proximal segment 60, and enter proximal end 104 of distal segment 62.

In the configuration shown in FIG. 2, proximal ends 82 and 84 are respectively coupled to a deflection knob 94 in handle 32. As described hereinbelow, medical professional 34 can manipulate knob 94 in order to control a deflection of distal segment 62 in a two-dimensional plane 96 which corresponds to the plane of the paper.

In the configuration shown in FIG. 2, handle 32 comprises a housing 114 that contains two rack gear channels 116. Preferably, rack gear channels 116 are located in opposite quadrants within the housing 114. A rack gear 118 can be slidably mounted within each rack gear channel 116. Each rack gear 118 is generally rectangular and has teeth 120 along the length of its interior edge. Between the rack gears 118 is a spur gear 122, also having teeth 124. Teeth 124 of spur gear 122 receive teeth 120 of rack gears 118 such that proximal movement of one of the rack gears results in distal movement of the other rack gear.

Proximal ends 82 and 84 of puller wires 78 and 80 are respectively attached to the distal ends of rack gears 118 by a puller wire coupling 126. Coupling 126 may be integral with rack gears 118 or fixedly attached to the rack gears. Each rack gear 118 may be soldered or glued to the coupling 126, for example, with polyurethane or epoxy. Alternatively, the proximal end of each puller wire coupling 126 may comprise a threaded hole to receive a threaded post at the distal end of the corresponding rack gear 118. Couplings 126 can be made of any suitable material, such as aluminum, brass, or stainless steel.

Deflection knob 94 extends around the circumference of the handle housing 114, allowing medical professional 34 to manipulate the knob no matter how handle 32 is rotated. If deflection knob 94 is moved proximally, the corresponding rack gear 118 moves in a proximal direction, which results in the attached puller wire to be pulled proximally. This causes the distal segment 62 to deflect in the direction of the quadrant of the lumen in the distal segment through which that puller wire extends.

Conversely, if the deflection knob 94 is pushed distally, the corresponding rack gear 118 moves distally. As a result, the opposite rack gear 118 moves proximally, pulling the corresponding puller wire and deflecting distal segment 62 in the opposite direction.

In the configuration shown in FIG. 2, electrode 46 is affixed to a distal tip 98 of distal segment 62. Electrode 46 is connected to control console 24 by wires (not shown) running through an additional lumen (not shown) in insertion tube 30. As described supra, system 20 can use electrode 46 for tasks such as determining a location of distal end 36 and measuring electrical activity of heart 26. In some embodiments, tubes 66, and the additional tubular structure whose respective lumen may contain one or more function elements (e.g., additional wires, cables and irrigation lines) may be twisted around each other within proximal segment 60.

Figure 3:
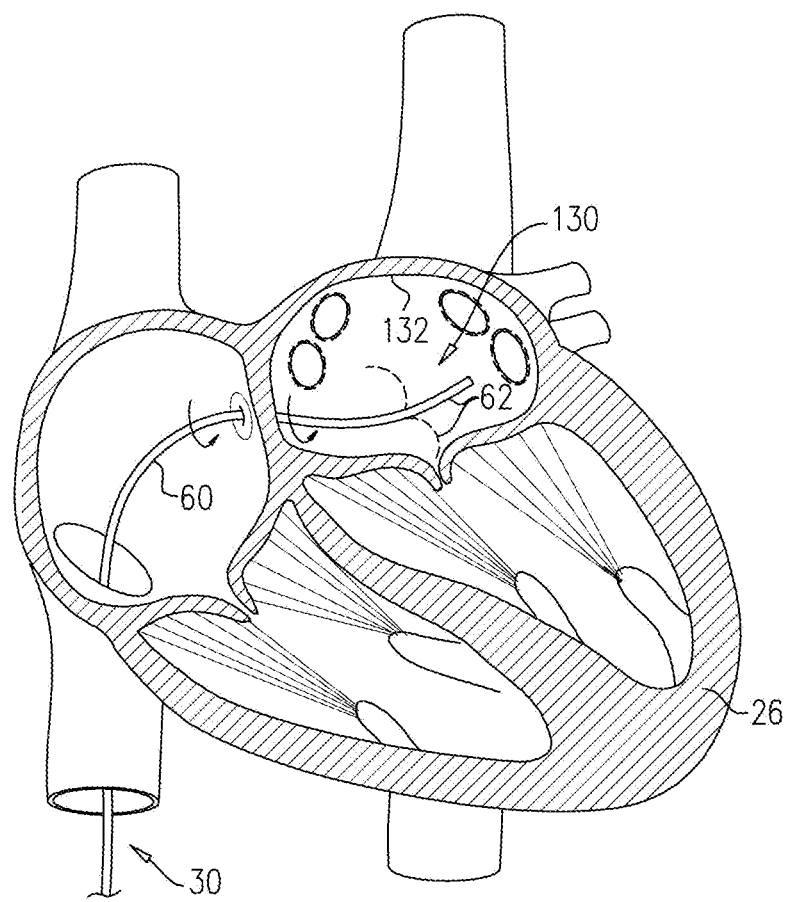
FIG. 3 is a schematic pictorial illustration of the deflectable section inside a cardiac chamber, in accordance with an embodiment of the present invention.

FIG. 3 is a schematic detail view of distal segment 62 in a chamber 130 of heart 26, in accordance with an embodiment of the present invention. When positioning distal tip to engage any intracardiac tissue 132 in chamber 130, medical professional can rotate handle 32 to rotate insertion tube 30, and can manipulate knob 94 to deflect (i.e., bend) distal segment 62. As described supra, proximal segment 60 is rotationally symmetrical since the proximal segment comprises wire 78 and compression coil 74 twisted around wire 80 and compression coil 76. Therefore, even when bent, the distal segment typically has minimal whipping when the operator rotates handle 32.

In some configurations, the twists per inch (TPI) of coils 74 and 76 can be in the range of 0.5-2.0 twists per inch. During a medical procedure, the bend that proximal segment 60 needs to traverse is typically relatively gentle compared to the bend in deflectable segment 62. For example, in some medical procedures, probe 22 traverses the inferior vena cava. In order to gain trans-septal access to the left atrium, the probe needs to turn 90 degrees. If the medical professional then wants probe 22 to enter the left ventricle, this can require an additional 90 degree turn.

A "tight" bend radius for proximal segment 60 segment may be approximately one inch. In this scenario, a 90 degree turn (i.e., a quarter of a circle) requires a path length of approximately 1.6 inches. In the lowest twisting of the puller wires and compression coils (i.e., 0.5 TPI), there would still be more than half a twisting period in the 90 degree turn. Therefore, over part of the turn the puller wires would be biased to preferentially bend in that direction, and over another part of the turn, the puller wires would be biased to preferentially bend in the opposite direction.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical probe, comprising:
a flexible insertion tube comprising a proximal segment and a deflectable distal segment, and containing first and second lumens running longitudinally through the insertion tube, wherein the first and second lumens are twisted only around each other in the proximal segment, and run parallel to each other in the deflectable distal segment; and
first and second wires running respectively through the first and second lumens and comprising respective first and second distal ends, which are anchored within the deflectable distal segment of the insertion tube.

2. The medical probe according to claim 1, and comprising first and second compression coils that respectively contain the first and the second wires, and respectively comprise the first and the second lumens.

3. The medical probe according to claim 2, and comprising first and second tubular structures that respectively contain the first and the second compression coils.

4. The medical probe according to claim 1, and comprising a third lumen running longitudinally through the insertion tube, wherein the first lumen, the second lumen and the third lumen are twisted around each other in the proximal segment.

5. The medical probe according to claim 4, and comprising one or more functional elements running through the third lumen, wherein a given functional element is selected from a list consisting of an additional wire, a cable, and an irrigation line.

6. The medical probe according to claim 1, wherein pulling on each of the first and second wires deflects the deflectable distal segment in different respective directions.

7. The medical probe according to claim 6, wherein the first and second lumens twisted around each other in the proximal segment limit whipping of the probe as it is rotated.

8. The medical probe according to claim 6, wherein the first and the second wires comprise respective first and second proximal ends; and comprising a handle coupled to the first and second proximal ends in order to control the pulling on the wires.

9. The medical probe according to claim 6, wherein the deflection is in a two-dimensional plane.

10. The medical probe according to claim 1, wherein the first and second distal ends of the wires are respectively anchored at different, respective points within the deflectable distal segment of the insertion tube.

11. A method for fabricating a medical probe, comprising:
providing a flexible insertion tube comprising a proximal segment and a deflectable distal segment, and containing first and second lumens running longitudinally through the insertion tube, wherein the first and second lumens are twisted only around each other in the proximal segment, and run parallel to each other in the deflectable distal segment; and
running first and second wires respectively through the first and second lumens, the first and the second wires having respective first and second distal ends, which are anchored within the deflectable distal segment of the insertion tube.

12. The method according to claim 11, and comprising providing first and second compression coils that respectively contain the first and the second wires, and respectively comprise the first and the second lumens.

13. The method according to claim 12, and comprising providing first and second tubular structures that respectively contain the first and the second compression coils.

14. The method according to claim 11, and comprising running a third lumen longitudinally through the insertion tube, wherein the first lumen, the second lumen and the third lumen are twisted around each other in the proximal segment.

15. The method according to claim 14, and comprising running one or more functional elements through the third lumen, wherein a given functional element is selected from a list consisting of an additional wire, a cable, and an irrigation line.

16. The method according to claim 11, wherein pulling on each of the first and second wires deflects the deflectable distal segment in different respective directions.

17. The method according to claim 16, wherein the first and second lumens twisted around each other in the proximal segment limit whipping of the probe as it is rotated.

18. The method according to claim 16, wherein the first and the second wires comprise respective first and second proximal ends; and the medical probe comprises a handle coupled to the first and second proximal ends in order to control the pulling on the wires.

19. The method according to claim 16, wherein the deflection is in a two-dimensional plane.

20. The method according to claim 11, and comprising respectively anchoring a first distal end of the first wire and a second distal end of the second wire at different, respective points within the deflectable distal segment of the insertion tube.

* * * * *